United States Patent
Dunaief

(10) Patent No.: US 8,501,789 B2
(45) Date of Patent: Aug. 6, 2013

(54) USE OF SALICYLALDEHYDE ISONICOTINOYL HYDRAZONE (SIH) FOR PROTECTION AGAINST RETINAL DISEASE

(75) Inventor: Joshua L. Dunaief, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1139 days.

(21) Appl. No.: 12/010,090

(22) Filed: Jan. 18, 2008

(65) Prior Publication Data

US 2008/0279913 A1 Nov. 13, 2008

Related U.S. Application Data

(60) Provisional application No. 60/881,154, filed on Jan. 19, 2007.

(51) Int. Cl.
*A61K 31/44* (2006.01)

(52) U.S. Cl.
USPC .......................................... 514/354; 514/912

(58) Field of Classification Search
USPC .................................................. 514/354, 912
See application file for complete search history.

(56) References Cited

U.S. PATENT DOCUMENTS

| | | | | |
|---|---|---|---|---|
| 2002/0086013 | A1* | 7/2002 | King | 424/143.1 |
| 2010/0004204 | A1* | 1/2010 | Franz et al. | 514/64 |

FOREIGN PATENT DOCUMENTS

WO WO 9841198 A1 * 9/1998

OTHER PUBLICATIONS

Battisti et al., Cell response to oxidative stress induced apoptosis in patients with Leber's hereditary optic neuropathy, J Neurol Neurosurg Psychiatry. Dec. 2004;75(12), printed from http://www.ncbi.nlm.nih.gov/pubmed/15548492, Abstract only, 1 page.* www.WebMD.com, Retinal Detachment—Treatment Overview, Aug. 26, 2009, printed from http://www.webmd.com/eye-health/tc/retinal-detachment-treatment-overview, 2 pages.*

Shen et al., Oxidative damage is a potential cause of cone cell death in retinitis pigmentosa, Journal of Cellular Physiology vol. 203, Issue 3, Jun. 2005, printed from http://onlinelibrary.wiley.com/doi/10.1002/jcp.20346/abstract;jsessionid=B2023772B90906B2C47B440F7451DF98.d02t01, Abstract only, 1 page.*

Merck Manuals, Hereditary Optic Neuropathies, 2005, http://www.merck.com/mmpe/print/sec09/ch107/ch107b.html, printed May 27, 2008, 2 pages.*

Merck Manuals, Retinitis Pigmentosa, 2005, http://www.merck.com/mmpe/print/sec09/ch106/ch106h.html, printed May 27, 2008, 2 pages.*

Schmidt-Erfuth et al., Management of neovascular age-related macular degeneration, 2007, Progress in Retinal and Eye Research, 26, 437-451.*

Mayo Clinic, Stargardt's disease: Can it be treated?, 2006, printed May 27, 2008, MayoClinic.com, http://www.mayoclinic.com/print/stargardts-disease/AN00846/METHOD=print, 2 pages.*

Thompson et al., Vitrectomy for the Treatment of Submacular Hemorrhages From Macular Degeneration: A Comparison of Submacular Hemorrhage/Membrane Removal and Submacular Tissue Plasminogen Activator—Assisted Pneumatic Displacement, Trans Am Ophthalmol Soc. Dec. 2005; 103: 98-107.*

(Continued)

*Primary Examiner* — Gigi Huang
(74) *Attorney, Agent, or Firm* — Mark S. Cohen; Pearl Cohen Zedek Latzer, LLP

(57) ABSTRACT

This invention relates to methods for treating age-related macular degeneration, blindness or glaucoma using an iron-chelator SIH.

3 Claims, 12 Drawing Sheets

OTHER PUBLICATIONS

Cicik et al., Interleukin-8, Nitric Oxide and Glutathione Status in Proliferative Vitreoretinopathy and Proliferative Diabetic Retinopathy, Ophthalmic Res 2003;35, printed from http://content.karger.com/produktedb/produkte.asp?typ=pdf&file=ORE2003035005251, Abstract only, 2 pages.*

Phillips et al., Increased breath biomarkers of oxidative stress in diabetes mellitus, Clin Chim Acta. Jun. 2004;344(1-2), printed from http://www.ncbi.nlm.nih.gov/pubmed/15149888, Abstract only, 1 page.*

Wang, Age-related Macular Degeneration, www.discoverymedicine.com, Dec. 11, 2009, printed from http://www.discoverymedicine.com/Wei-Wang/2009/12/11/age-related-macular-degeneration-4/, 7 pages.*

Abuchowski et al. "Immunosuppressive Properties and Circulating Life of Achromobacter Glutaminase-Asparaginase Covalently Attached to Polyethylene Glycol in Man" Cancer Treat Rep. 65(11-12): 1077-81 1981.

Katre et al. "Chemical modification of recombinant interleukin 2 by polyethylene glycol increases its potency in the murine Meth A sarcoma model" Proc Natl Acad Sci U S A. 84(6):1487-91. Mar. 1987.

Conrad et al., Biol. Proced. Online 2000;2:39-45, Post-Electrophoretic Identification of Oxidized Proteins.

Horackova et al., "The antioxidant effect of a noval iron chelator salicylaldehyde isonicotinoyl hydrazone in the prevention of $H_2O_2$ injury in adult cardiomyocytes", Cardiovascular Research 47, 2000, 529-536.

Simunek et al., "SIH—a noval lipophilic iron chelator—protects H9c2 cardiomyoblasts from oxidative stress-induced mitochondrial injury and cell death", Journal of Molecular and Cellular Cardiology 39, 2005, 345-354.

Lesnikov et al., "Protection of human and murine hepatocytes against Fas-induced death by transferrin and iron", Apoptosis 2006, 11:79-86.

Creighton-Gutteridge et al., "A novel iron chelator that does not induce HIF-1 activity", Free Radical Biology & Medicine, vol. 33, No. 3, pp. 356-363, 2002.

Zhang et al., "Intracellular kinetics of iron in reticulocytes: evidence for endosome involvement in iron targeting to mitochondria", Blood, Jan. 1, 2005, vol. 105, No. 1.

Ponka et al., "Acquisition of Iron from Transferrin Regulates Reticulocyte Heme Synthesis", The Journal of Biological Chemistry, vol. 260, No. 27, Issue of Nov. 25, pp. 14717-14721, 1985.

* cited by examiner

USE OF SALICYLALDEHYDE ISONICOTINOYL HYDRAZONE (SIH) FOR PROTECTION AGAINST RETINAL DISEASE

CROSS REFERENCE TO RELATED APPLICATION(S)

This application claims priority from U.S. Provisional Application Ser. No. 60/881,154 filed Jan. 19, 2007, which is incorporated herein by reference in its entirety.

GOVERNMENT INTEREST

This invention was supported, in part, by Grant Number EY015240, from the NIH. The government may have certain rights in the invention

FIELD OF THE INVENTION

This invention is directed to methods for protecting retinal cells using an iron-chelator or SIH. Specifically, the invention relates to methods and compositions for treating or preventing age-related macular degeneration, blindness or glaucoma using an iron-chelator or SIH.

BACKGROUND OF THE INVENTION

Iron is essential for life due to its role in one-electron redox chemistry in the electron transport chain and as a cofactor in heme and iron-sulfur cluster containing proteins. However, it also represents a potentially dangerous electron-transporting catalytic system that is able to induce oxidative damage through the Fenton reaction. In the Fenton reaction, iron reacts with hydrogen peroxide ($H_2O_2$) to produce hydroxyl radical, the most reactive and toxic of the reactive oxygen species (ROS). Iron is prevented from reacting with $H_2O_2$ by storage within proteins such as ferritin. At the same time a small amount of redox-active iron exists in the intracellular labile iron pool, making this accessible ferrous iron dangerous under conditions of cellular oxidative stress. Moreover, superoxide and $H_2O_2$ are able to release iron from its storage proteins, increasing the labile iron pool and creating a vicious cycle of ROS production.

Elevated iron levels are found in the retinas of patients with age-related macular degeneration, suggesting that iron may play a role in the pathogenesis of AMD. Likewise, patients with the rare hereditary disease aceruloplasminemia have iron overload of the brain, retina, and pancreas, leading to degeneration in these organs. The retinal degeneration in these patients resembles an early onset form of the blinding disease age-related macular degeneration (AMD).

AMD causes severe, irreversible vision loss and is the leading cause of blindness in individuals older than 50 years in the Western World. Macular degeneration is a clinical term that is used to describe a family of diseases that are all characterized by a progressive loss of central vision associated with abnormalities of Bruch's membrane, the choroid, the neural retina and/or the retinal pigment epithelium. These disorders include very common conditions that affect older subjects (age-related macular degeneration or AMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease, and Malattia Leventinese Age-related macular degeneration (AMD), the most prevalent macular degeneration, is associated with progressive diminution of visual acuity in the central portion of the visual field, changes in color vision, and abnormal dark adaptation and sensitivity. Two principal clinical manifestations of AMD have been described as the dry, or atrophic, form, and the wet, or exudative, form. The most significant risk factor for the development of both forms are age and the deposition of drusen, abnormal extracellular deposits, behind the retinal pigment epithelium (RPE). Drusen causes a lateral stretching of the RPE monolayer and physical displacement of the RPE from its immediate vascular supply, the choriocapillaris. This displacement creates a physical barrier that may impede normal metabolite and waste diffusion between the choriocapillaris and the retina.

Thus, identification and use of survival-promoting factors for the retinal pigment epithelium (RPE), would potentially be of great importance for the treatment and prophilaxis of pathological conditions which result in blindness due to apoptosis of the RPE.

SUMMARY OF THE INVENTION

In one embodiment, the invention provides a method of treating an oxidative stress of the retina in a subject, comprising contacting the retina with an effective amount of a metal chelator, wherein said chelator is salicylaldehyde isonicotinoyl hydrazone (SIH), pyridoxal isonicotinoyl hydrazone (PIH), N-(2-hydroxybenzyl)-L-serine (HBSer), desferrioxamine (DF) or a combination thereof, thereby removing a metal causing the oxidative stress.

In another embodiment, provided herein is the use of a metal chelator wherein said metal chelator is salicylaldehyde isonicotinoyl hydrazone (SIH), pyridoxal isonicotinoyl hydrazone (PIH), N-(2-hydroxybenzyl)-L-serine (HBSer), desferrioxamine (DF) or a combination thereof in a composition for the treatment of an oxidative stress of the retina in a subject, comprising an effective amount of said chelator.

In one embodiment, provided herein is a method for preventing apoptosis of retinal cells in a subject, comprising contacting said retinal cells with an effective amount of a metal chelator, wherein said metal chelator is salicylaldehyde isonicotinoyl hydrazone (SIH), pyridoxal isonicotinoyl hydrazone (PIH), N-(2-hydroxybenzyl)-L-serine (HBSer), desferrioxamine (DF) or a combination thereof thereby removing iron causing oxidative stress leading to apoptosis of retinal cells.

In another embodiment, provided herein is a method of treating diabetic retinopathy in a subject, comprising the step of administering to the subject a composition comprising an effective amount of salicylaldehyde isonicotinoyl hydrazone (SIH), pyridoxal isonicotinoyl hydrazone (PIH), or a combination thereof.

In one embodiment, provided herein is a method of treating retinal detachment in a subject, comprising the step of administering to the subject a composition comprising an effective amount of salicylaldehyde isonicotinoyl hydrazone (SIH), pyridoxal isonicotinoyl hydrazone (PIH), or a combination thereof.

In another embodiment, provided herein is a method of treating subretinal hemorrhage in a subject, comprising the step of administering to the subject a composition comprising an effective amount of salicylaldehyde isonicotinoyl hydrazone (SIH), pyridoxal isonicotinoyl hydrazone (PIH), or a combination thereof.

In one embodiment, provided herein is a method of treating glaucoma in a subject, comprising the step of administering to the subject a composition comprising an effective amount of salicylaldehyde isonicotinoyl hydrazone (SIH), pyridoxal isonicotinoyl hydrazone (PIH), or a combination thereof.

In another embodiment, provided herein is a method of preventing apoptosis in a retinal pigment epithelial cell (RPE), caused by an agent, comprising the step of contacting the retinal pigment epithelial cell (RPE) with a composition comprising salicylaldehyde isonicotinoyl hydrazone (SIH), pyridoxal isonicotinoyl hydrazone (PIH), or a combination thereof, thereby reducing oxidative stress.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

Figure 1:
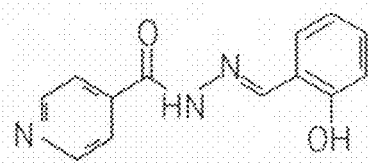
FIG. 1 shows the structure of Salicylaldehyde Isonicotinoyl Hydrazone (SIH)

This invention relates in one embodiment to methods for treating age-related macular degeneration, blindness or glaucoma using an iron-chelator or SIH (See e.g. FIG. 1).

In one embodiment, iron is known to cause oxidative stress. Elevated iron levels are found in the retinas of patients with age-related macular degeneration, suggesting that iron may play a role in the pathogenesis of AMD. In one embodiment, certain chelators are effective in reducing iron levels in various cell types, including RPE cells; In another embodiment, iron chelation confers cytoprotection against oxidative damage in cardiac myocytes.

In one embodiment, the chelators most effective at reducing iron levels in RPE cells and their optimal doses are provided herein, and the protective effects of iron chelation against oxidative stress in the human retinal pigment epithelium are described.

In one embodiment, generation of reactive oxygen species (ROS) is associated with cell death, functioning as effectors in apoptotic pathways. In another embodiment, iron is a potent generator of ROS, and iron-generated ROS within mitochondria and lysosomes promote cell death. In one embodiment, the iron chelators described herein, and used in the methods provided herein can protect cells from death induced by exogenous oxidants. In one embodiment, lipophilic, cell membrane-permeable chelator, salicylaldehyde isonicotinoyl hydrazone (SIH) in one embodiment, or pyridoxal isonicotinoyl hydrazone (PIH) or their combination in other embodiments, is effective in protecting RPE cells from death induced by agents that are not ROS themselves, but rather may cause the cell to produce iron-catalyzed ROS as part of the mechanism of cell death induction.

In one embodiment, provided herein, is a method of treating an oxidative stress of the retina in a subject, comprising contacting the retina with an effective amount of a metal chelator wherein said chelator is salicylaldehyde isonicotinoyl hydrazone (SIH), pyridoxal isonicotinoyl hydrazone (PIH), N-(2-hydroxybenzyl)-L-serine (HBSer), desferrioxamine (DF) or a combination thereof, thereby removing a metal causing the oxidative stress.

In one embodiment, the term "oxidative stress" refers to the steady-state level of oxidative damage within a cell, tissue or organism caused by reactive oxygen species (ROS). Oxidants are produced as part of the normal metabolism of all cells but also are an important component of the pathogenesis of many disease processes. Reactive oxygen species (ROS), in one embodiment, are critical elements of the pathogenesis of diseases of the lung, the central nervous system and skeletal muscle. In one embodiment, ROS are critical in the pathological development of diseases associated with retinal cells, such as, in another embodiment, with RPE cells.

Redox homeostasis refers in one embodiment to the normal physiologic process of reduction and oxidation in order to remove unstable, damaging, reduced, reactive oxygen species (ROS) which may include in certain embodiments the following oxygen free radicals ($O_2.$—superoxide, $H_2O_2$—hydrogen peroxide, —OH. hydroxyl radical, and singlet oxygen) and organic analogues which include reactive nitrogen species (RNS) primarily peroxynitrite $ONOO..$.

Figure 2:
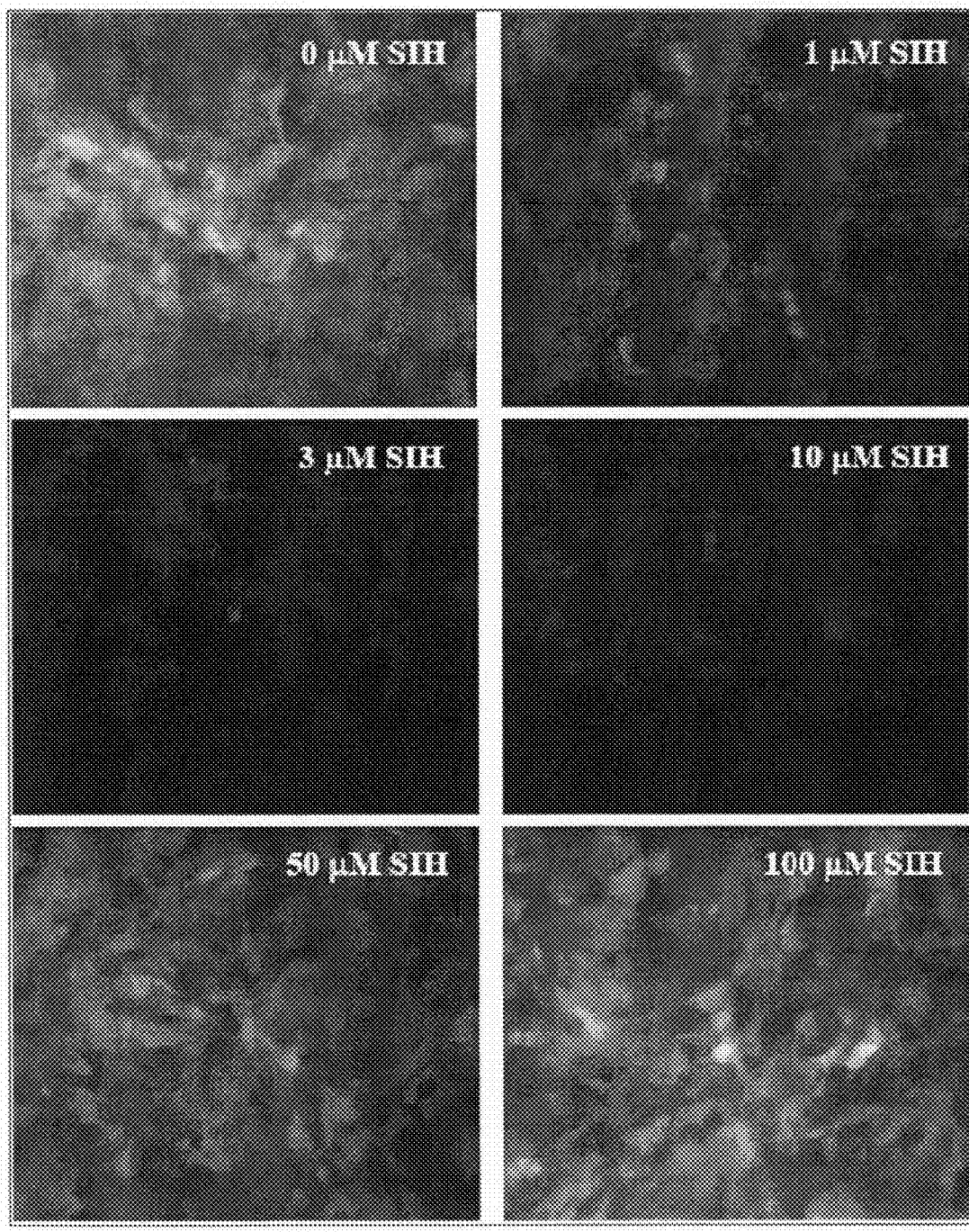
FIG. 2 shows fluorescence photomicrographs of intracellular labile iron levels in ARPE-19 cells stably transfected with the IRE-GFP reporter (iRPE) cells. Fluorescence intensity indicates relative intracellular iron levels. Cells were incubated for 24 h with HBSS (control) or different concentrations of SIH in HBSS as indicated on the images. Images are representative of results from 3 independent experiments and taken using identical exposure parameters.

In one embodiment, the retina, being exposed to both sunlight and air, as well as being abundent in polyunsaturated fatty acids, making it a favorable environment for the generation of reactive oxygen species (ROS). In another embodiment, retinal pigment epithelium (RPE) generates a number of reactive oxygen species when illuminated with light. In another embodiment, phagocytosis of photoreceptor outer segments by RPE causes an increase in intracellular and extracellular $H_2O_2$ generation. In one embodiment, SIH protects RPE from lipid peroxidation generated due to light and exposure to air (FIGS. 1 and 2)

Since the RPE plays a role in transporting selective molecules between the choroidal blood and the neural retina, which forms the outer blood-retinal barrier, dysfunction or death of the RPE cells will induce degeneration of photoreceptors in certain embodiments. Several factors may contribute to the pathogenesis of AMD, all of which may involve the RPE: a decrease in the number of RPE cells in the macular area, accumulation of degenerated substance (drusen) in the inner layer of Bruch's membrane, and leakage at the Bruch's membrane of the macula, which may result in subretinal neovascularization. In one embodiment, SIH used in the methods and compositions described herein, inhibits the production of ROS in RPE, thereby inhibiting the development, or in another embodiment, the progression of AMD or cataract.

In one embodiment, ferrous iron ($Fe^{2+}$) generates free radicals that can cause oxidative damage via the Fenton reaction. in another embodiment, iron overload causes retinal degenerations. In one embodiment, iron retained in the eye as a foreign body or injected into the vitreous causes photoreceptor degeneration, demonstrating that iron overload is toxic to photoreceptors. Therefore, iron chelators such as in one embodiment, SIH, may be used to remove iron as a catalyst for the generation of ROS in RPE.

Surprisingly, in one embodiment, cells contacted with SIH at higher doses, 50 µM and 100 µM, increase labile iron pool than cells contacted with the 3 and 10 µM SIH doses, reflecting an ability of high concentrations of SIH to increase the labile iron pool by mobilizing iron stores in one embodiment or removing iron from iron-binding proteins in another embodiment. In one embodiment, the therapeutically effective amount of the iron-chelator used in the compositions and methods described herein is adjusted such that there is no increase in labile iron pool.

In another embodiment, the compositions described herein are administered to the subject as a prophilactic measure prior to a known exposure to conditions suspected in increasing the risk of causing RPE cell death. In one embodiment, the compositions described herein are administered about 4 hours pre-exposure.

In one embodiment, iron overload is also implicated in the retinal degeneration occurring in patients with the rare autosomal recessive disease aceruloplasminemia. These patients have pathologic accumulation of iron in liver, spleen, pancreas, retina, and basal ganglia by the fourth or fifth decade of life.

In one embodiment, the oxidative stress for which the iron chelator in the methods and copositions described herein, causes age-related macular degeneration, diabetic retinopathy, retinal detachment, subretinal hemorrhage, glaucoma or a combination thereof. In another embodiment, the oxidative stress results in apoptosis of retinal cell. In one embodiment, iron chelator used in the methods and copositions described herein is salicylaldehyde isonicotinoyl hydrazone (SIH), pyridoxal isonicotinoyl hydrazone (PIH), N-(2-hydroxybenzyl)-L-serine (HBSer), desferrioxamine (DF) or a combination thereof. In one embodiment, each caused pathology is a separate embodiment.

Therefore, according to this aspect of the invention, provided herein is a method of treating glaucoma in a subject, comprising the step of administering to the subject a composition comprising an effective amount of salicylaldehyde isonicotinoyl hydrazone (SIH), pyridoxal isonicotinoyl hydrazone (PIH), or a combination thereof, or in another embodiment, a method of treating diabetic retinopathy in a subject, comprising the step of administering to the subject a composition comprising an effective amount of salicylaldehyde isonicotinoyl hydrazone (SIH), pyridoxal isonicotinoyl hydrazone (PIH), or a combination thereof, wherein in one embodiment, the oxidative stress results in apoptosis of retinal cells, and treating comprises reducing incidence, or inhibiting, suppressing or a combination thereof, or wherein treating results in reducing symptoms, ameliorating symptoms, delaying onset, preventing onset, curing said pathology or a combination thereof in other embodiments.

In one embodiment, the methods and compositions described herein are effective in the treatment of diabetic retinopathy. Sight-threatening diabetic retinopathy is one of the most common complications of diabetes and is the most common cause of vision loss in the under 65 years age group in developed countries, as a result of non-resolving vitreous hemorrhage, traction retinal detachment or diabetic maculopathy. Sight-threatening diabetic retinopathy refers in one embodiment to diabetic complications affecting the retina that predictably lead to severe loss of vision. These changes include non-resolving vitreous hemorrhage, tractional retinal detachment, or retinal edema.

A 2.5 fold increase of iron in the vitreous compared to macular hole was shown to occur in one embodiment in proliferative diabetic retinopathy. In another embodiment, Iron mediates the formation of protein dicarbonyls, and it is increased carbonyl stress in diabetes which leads in one embodiment to increased accumulation of AGE in long and short-lived proteins thereby affecting their normal function. In one embodiment, the methods and compositions described herein remove excess metals, such as Cu+2 and Fe+2 from the vitreous, leading to restoration of oxidative homeostasis in subjects with diabetic retinopathy (DR), thus treating DR.

In one embodiment, the methods and compositions described herein, are used to prophylactically treat retinal detachment, or retinal edema. Retinal detachment is characterized in one embodiment, by abnormal accumulation of fluid in the subretinal space leading to detachment of the retina from the underlying retinal pigment epithelium (RPE). Retinal edema refers to abnormal accumulation of fluid within the retina itself. Retinal detachment or edema in the central part of the retina (macula) produces significant loss of vision, and can ultimately lead to irreversible blindness. A wide variety of ocular pathologies can result in retinal detachment or retinal edema. The most common type of retinal detachment is rhegmatogenous retinal detachment, which occurs as a result of single or multiple tears or holes in the retina that permit liquefied vitreous to enter into the subretinal space and create a retinal detachment. In one embodiment, iron catalyzes the oxidation of the polyunsaturated fatty acids (PUFA) with which the retina is rich, leading to degeneration of the detached retina.

In one embodiment, the exudative form of AMD is characterised by subretinal haemorrhage, and the methods and compositions described herein may be used in the inhibition and prevention of subretinal haemorrhage.

In another embodiment, the methods and compositions described herein, may be used in the treatment of Glaucoma. In one embodiment, the term "glaucoma" refers to a group of ocular disorders, characterized by degeneration of the optic nerve. The disease is characterized by a death of ganglion cells in the retina (RGCs). As ganglion cell axons form the optic nerve and bring visual information to the brain, their death directly affects visual performance. The best characterized forms of glaucoma are associated with elevations in intraocular pressure mainly due to a decrease in the rates of aqueous humor drainage through the aqueous drainage channels.

Primary congenital or infantile glaucoma is an inherited disorder that is characterized by an improper development of the aqueous outflow system of the eye, which leads to elevated intraocular pressure, enlargement of the glove or cornea (i.e., buphthalmos), damage to the optic nerve, and eventual visual impairment. Primary open angle glaucoma (POAG) is a disorder characterized in one embodiment, by atrophy of the optic nerve resulting in visual field loss and eventual blindness. POAG has been divided into two major groups, based on age of onset and differences in clinical presentation. In one embodiment, Juvenile-onset POAG manifests itself in late childhood or early adulthood. Its progression is rapid and severe, with high intraocular pressure. This type of POAG is poorly responsive to medical treatment, and usually requires ocular surgery. In another embodiment, Adult- or late-onset POAG is the most common type of glaucoma. It is milder and develops more gradually than juvenile-onset POAG, with variable onset usually after the age of 40. This type of POAG is associated with slight to moderate elevation of intraocular pressure, and often responds satisfactorily to regularly monitored medical treatment. Unfortunately, this disease may not be detected until after irreversible damage to the optic nerve has already occurred because it progresses gradually and painlessly.

In one embodiment, the term "treatment", or "treating" refers to any process, action, application, therapy, or the like, wherein a subject, including a human being, is subjected to medical aid with the object of improving the subject's condition, directly or indirectly. The term "treating" refers also to reducing incidence, or alleviating symptoms, eliminating recurrence, preventing recurrence, preventing incidence, improving symptoms, improving prognosis or combination thereof in other embodiments.

"Treating" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent incidence of age-related macular degeneration, diabetic retinopathy, retinal detachment, subretinal hemorrhage, glaucoma or a combination thereof. The alleviation of a condition that results in a more serious condition is encompassed by this term. Therefore, in one embodiment, provided herein a method of treating age-related macular degeneration, diabetic retinopathy, retinal detachment, subretinal hemorrhage, glaucoma or a combination thereof, due to an oxidative stress of the retina in a subject, comprising contacting the retina with an effective amount of a metal chelator wherein said chelator is salicylaldehyde isonicotinoyl hydrazone (SIH), pyridoxal isonicotinoyl hydrazone (PIH), N-(2-hydroxybenzyl)-L-serine (HBSer), desferrioxamine (DF) or a combination thereof, thereby removing a metal causing the oxidative stress.

In one embodiment, the methods described hereinabove, make usage of the compositions described herein. In another embodiment, provided herein is use of a chelator wherein said chelator is salicylaldehyde isonicotinoyl hydrazone (SIH), pyridoxal isonicotinoyl hydrazone (PIH), N-(2-hydroxybenzyl)-L-serine (HBSer), desferrioxamine (DF) or a combination thereof in a composition for the treatment of an oxidative stress of the retina in a subject, comprising an effective amount of said chelator. In another embodiment, the composition for the treatment of an oxidative stress of the retina in a subject described hereinbelow, are used in the methods provided herein and make use of the metal chelators described herein.

In one embodiment, the compositions described herein use isonicotinoyl hydrazone (SIH) in a composition for the treatment of an oxidative stress of the retina in a subject, comprising an effective amount of said chelator. In one embodiment, the oxidative stress sought to be treated using the compositions and methods provided herein, causes apoptosis of retinal cells, or age-related macular degeneration, diabetic retinopathy, retinal detachment, subretinal hemorrhage, glaucoma or a combination thereof, in other embodiments.

In one embodiment, the compositions described herein, used in the invention further comprise a carrier, or excipient, lubricant, flow aid, processing aid or diluent in other embodiments, wherein the carrier, excipient, lubricant, flow aid, processing aid or diluent is a gum, starch, a sugar, a cellulosic material, an acrylate, calcium carbonate, magnesium oxide, talc, lactose monohydrate, magnesium stearate, colloidal silicone dioxide or mixtures thereof.

In another embodiment, the composition further comprises a binder, a disintegrant, a buffer, a protease inhibitor, a surfactant, a solubilizing agent, a plasticizer, an emulsifier, a stabilizing agent, a viscosity increasing agent, a sweetner, a film forming agent, or any combination thereof.

In one embodiment, the composition is a particulate composition coated with a polymer (e.g., poloxamers or poloxamines). Other embodiments of the compositions of the invention incorporate particulate forms protective coatings, protease inhibitors or permeation enhancers for various routes of administration, including parenteral, opthalmic and oral. In one embodiment the pharmaceutical composition is administered parenterally, transmucosally, transdermally, intravenously, intradermally, subcutaneously, intraventricularly, or intracranially.

In one embodiment, the compositions of this invention may be in the form of a pellet, a tablet, a capsule, a solution, a suspension, a dispersion, an emulsion, an elixir, a gel, an ointment, a cream, or a suppository.

In another embodiment, the composition is in a form suitable for oral, intravenous, parenteral, transmucosal, transdermal, or topical administration. In one embodiment the composition is a controlled release composition. In another embodiment, the composition is an immediate release composition. In one embodiment, the composition is a liquid dosage form. In another embodiment, the composition is a solid dosage form.

In one embodiment, the term "pharmaceutically acceptable carriers" includes, but is not limited to, may refer to 0.01-0.1M and preferably 0.05M phosphate buffer, or in another embodiment 0.8% saline. Additionally, such pharmaceutically acceptable carriers may be in another embodiment aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

In one embodiment, the compounds of this invention may include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The pharmaceutical preparations of the invention can be prepared by known dissolving, mixing, granulating, or tablet-forming processes. For oral administration, the active ingredients, or their physiologically tolerated derivatives in another embodiment, such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the active ingredients or their physiologically tolerated derivatives such as salts, esters, N-oxides, and the like are converted into a solution, suspension, or emulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, and such organic bases as isopropylamine, trimethylamine, 2-ethylamino ethanol, histidine, procaine, and the like.

The active agent is administered in another embodiment, in a therapeutically effective amount. The actual amount administered, and the rate and time-course of administration, will depend in one embodiment, on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used in another embodiment, to deliver the active agent more specifically to certain types of cell, by the use of targeting systems such as antibodies or cell specific ligands. Targeting may be desirable in one embodiment, for a variety of reasons, e.g. if the agent is unacceptably toxic, or if it would otherwise require too high a dosage, or if it would not otherwise be able to enter the target cells.

Such compositions are in one embodiment liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms, protective coatings, protease inhibitors, or permeation enhancers for various routes of administration, including parenteral, pulmonary, nasal, and oral.

In one embodiment, the compositions described herein used in the methods described herein may be injected into the eye, for example, injection under the conjunctiva or tenon capsule, intravitreal administration (injection into the vitreous), or retrobulbar (behind the eyeball). The "vitreous body" is disposed within a posterior portion of the eye and occupies approximately four fifths of the cavity of the eyeball, behind the lens. The vitreous body is formed of gelatinous material, known as the vitreous humor. The vitreous humor of a normal human eye is made up of approximately 99% water along with 1% macromolecules including; collagen, hyaluronic acid, soluble glycoproteins, sugars and other low molecular weight metabolites. In one embodiment, the compositions described herein are injected into either a pseudophakic or a phakic eye, whereby the location of the injection posterior to the limbus will vary accordingly, either before, simultaneously or after injections with anti VEGF antibodies (e.e Avastin™), antibiotics and the like. In another embodiment, intravitreal injection of the compositions described herein, may be a preventative, curative or palliative in purpose, whereby each is a separate embodiment of the methods described herein.

The use of compositions described herein for administration in the methods of treatment described herein, is done in one embodiment via an ophthalmic solution. The solution comprises in one embodiment, aqueous solutions and water-miscible ointments in which the compositions of the invention may be dissolved or suspended in, in finely divided form. The aqueous solutions and suspensions may incorporate pharmaceutically acceptable auxiliary ingredients that are not incompatible with the compositions described herein. A suitable vehicle comprise in another embodiment, a simple physiological saline solution containing 0.9% sodium chloride by weight. Such a solution is isotonic with tear fluid and is therefore non-irritating to the eye. Other solutions or suspensions wherein the formulation including the compositions of the invention and other auxiliary ingredients is hypotonic may be adjusted in one embodiment, to isotonicity by addition of a tonicity adjusting agent, e.g., sodium chloride. In one embodiment, hypotonic and hypertonic solutions or suspensions are also used, and are also acceptable for compliant ocular use. The ophthalmic solutions and suspensions of the invention incorporate in another embodiment other auxiliary agents such as buffers to control the pH within the practical range for storing and applying topical ophthalmic compositions of the inventions, i.e, from about pH 3 to about pH 8.5. In one embodiment, a physiological saline solution is buffered with a suitable buffering agent, e.g., a phosphate buffer, to maintain approximately physiological pH. Such a solution is buffered in another embodiment, at a pH of 7.2-7.4 to match the natural pH of the tears bathing the anterior segment of the eyeball.

The ophthalmic solution or suspension may incorporate in another embodiment conventional ingredients to improve the comfort of the dosage form, e.g., demulcents, such as polysorbate 80, polyethylene glycol (PEG) 400, dextran 70, gelatin, glycerin, propylene glycol, and the like. The ophthalmic solution or suspension may contain viscosity increasing constituents such as methylcellulose, hydroxypropyl cellulose, hydroxypropyl methylcellulose, poly (vinylpyrrolidone), polyvinyl alcohol, and the like. Several of the viscosity-adjusting agents also exhibit a demulcent function. Many of the viscosity-adjusting agents, when used as constituents of suspensions or emulsions containing the active ingredient, act as suspending agents to retard settling of solid particles or as protective colloids for emulsions to prevent phase separation.

The ophthalmic vehicle, whether hydrophilic in one embodiment, or hydrophobic in another, may also incorporate conventional antimicrobial preservative agents in order to prevent contamination of multiple-dose packages of the ophthalmic medication such as dropping bottles, tubes of ointments or bottles with accompanying eyedroppers. Suitable preservatives include in one embodiment quaternary ammonium compounds, e.g., benzalkonium chloride, cetylpyridinium chloride and the like; ethyl paraben, propyl paraben; alcohols, such as benzyl alcohol; organomercurial compounds, such as thimerosal; polybiguanide compounds such as chlorhexidine digluconate, polyaminopropyl biguanide, and the like. A compound that promotes the permeation of the compositions of the invention into the ocular tissues, such as dimethyl sulfoxide, a quaternary ammonium compound, e.g., benzalkonium chloride, or an opthalmologically acceptable surfactant, e.g., disodium lauryl sulfosuccinate, or the like may also be incorporated into the ophthalmic vehicle. When the composition of the invention is administered in the form of a suspension in an aqueous medium the suspension may also contain a suspending agent, e.g., methyl cellulose, propylcellulose, carboxymethyl-cellulose, poly(vinylpyrrolidone), poly(vinyl alcohol), and the like.

In one embodiment, the usage of metal chelator, such as salicylaldehyde isonicotinoyl hydrazone (SIH) in one embodiment, pyridoxal isonicotinoyl hydrazone (PIH), N-(2-hydroxybenzyl)-L-serine (HBSer), desferrioxamine (DF) or a combination thereof in other embodiments, in the compositions described hereinabove, are used in the methods provided herein.

In one embodiment, provided herein, is a method for preventing apoptosis of retinal cells in a subject, comprising contacting said retinal cells with an effective amount of an iron chelator, wherein said iron chelator is salicylaldehyde isonicotinoyl hydrazone (SIH), pyridoxal isonicotinoyl hydrazone (PIH), N-(2-hydroxybenzyl)-L-serine (HBSer), desferrioxamine (DF) or a combination thereof, thereby removing iron causing oxidative stress leading to apoptosis of retinal cells.

RPE cells are subjected to oxidant insult from superoxide in one embodiment, or H2O2 produced by mitochondrial respiration and by photo-oxidation in other certain embodiments. This photo-oxidation is exacerbated in one embodiment, by the accumulation of age-pigment, or lipofuscin, in these post-mitotic cells. A major fluorophore of RPE lipofuscin is A2E. In one embodiment, A2E forms in photoreceptor cells from reactions of all-trans-retinal and phosphatidylethanolamine (PE) that generate the precursor A2PE. Within RPE lysosomes A2PE undergoes phosphate cleavage to generate A2E, which in one embodiment acts as a photosensitizer, causing production of ROS when exposed to blue light and in another embodiment, inducing apoptosis of RPE cells.

In addition to A2E-induced ROS production, in another embodiment, blue light induces chemical modifications to A2E itself, and in another embodiment, these products are subsequently toxic in the dark. In one embodiment, photolysis of A2E results in the formation of a series of higher-molecular-weight compounds, with each successive photoproduct larger than the previous one. In one embodiment, these are epoxides along the acyclic chain starting from epoxidation of the 7,8 and 7',8' double bonds, and in another embodiment, eventually forming a nonaepoxide that are toxic in the dark. In one embodiment, the compositions provided herein inhibit or suppress the formation of epoxides caused by UV sensitization of A2E.

In one embodiment, cell death triggered by UV radiation in A2E-laden RPE is decreased in the presence of the iron chelating agents described herein. Interestingly, SIH has a cytoprotective effect not only when cells are pre-administered the chelators provided herein before UV exposure, but also when the chelators described herein, used in the compositions described herein is administered about one hour after UV exposure.

In one embodiment, staurosporine and Fas in another embodiment, are two other agents that induce cell death in RPE cells. Staurosporine is a protein kinase C inhibitor that in one embodiment, rapidly increases mitochondrial production of ROS due to mitochondrial production of H2O2. RNAi-mediated knockdown of the mitochondrial peroxidase PrxIII increases susceptibility to staurosporine-induced death in one embodiment. In another embodiment, ectopic expression of the H2O2-degrading enzyme catalase in the mitochondria protects against staurosporine induced cell death. In another embodiment antioxidant compounds such as N-acetyl cysteine in one embodiment protects against staurosporine induced death.

In one embodiment, activation of the cell surface receptor Fas induces apoptosis in RPE cells and it plays a role in age-related macular degeneration and in another embodiment, increased levels H2O2 indicating that in certain embodiments H2O2 plays a role early in the apoptotic pathway induced by Fas. In one embodiment, the antioxidant glutathione protects cells from Fas triggered death. In another embodiment, treatment of cells with the antioxidant N-acetyl cysteine blocks Fas induced death by blocking ROS-mediated assembly of the apoptosome and is used in the methods and compositions described herein.

In one embodiment, the methods and compositions described herein, are effective in the protective mechanism of the compositions described hereinabove, is through blocking ROS production in mitochondria in response to induction of apoptosis.

In one embodiment, provided herein is a method of preventing apoptosis in a retinal pigment epithelial cell (RPE), caused by an agent, comprising the step of contacting the retinal pigment epithelial cell (RPE) with a composition comprising salicylaldehyde isonicotinoyl hydrazone (SIH), pyridoxal isonicotinoyl hydrazone (PIH), or a combination thereof, thereby reducing oxidative stress.

In another embodiment, the agent causing apoptosis in a retinal pigment epithelial cell (RPE), which is sought to be prevented using the methods described herein is hydrogen peroxide. In one embodiment the agent is staurosporine, or a Fas activator, A2E in combination with UV radiation, or their combination in other discrete embodiments of agents causing apoptosis in a retinal pigment epithelial cell (RPE).

In one embodiment, contacting the subject with the compositions described herein, in the methods provided is via oral administration, or in other embodiments via parenteral, intracavital, eye drops, subconjunctival injection, subconjunctival implant, intravitreal injection, intravitreal implant, sub-Tenon's injection, sub-Tenon's implant administration or their combination.

In one embodiment, the compositions described hereinabove, used in the compositions provided herein, further comprise an antioxidant, a UV adsorber or their combination. In another embodiment, the anti-oxidant is N-acetyl cystein, or mitochondrial peroxidase PrxIII, catalase, glutathione peroxidase, or their combination in other discrete embodiments of the antioxidants that are further comprised in the compositions used in the methods provided herein. In one embodiment, the UV adsorber is an aloe vera chromophore emollient, or ergosterol, 7-dehydrocholesterol, pre-ergocalciferol, precholecalciferol, 1α, 24-dihydroxy vitamin D, α calcidol, calcifedol, 1α,24,25-trihydroxy vitamin D, 1β,25-dihydroxy vitamin D, oxacalcitriol, calcipotriol, dihydrotachysterol, vitamin $K_1$, vitamin $K_2$, menadiol diphosphate, or their combination in other discrete embodiments of the UV adsorber that are further comprised in the compositions used in the methods provided herein.

In an Aloe Vera Chromophore Emollient

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods

Cell Culture

Human adult RPE cells (ARPE-19 cell line from ATCC) were cultured until confluent in 24-well Falcon plates in 1:1 DMEM High Glucose with L-Glutamine and Ham's F12 media (Invitrogen, Carlsbad, Calif.) supplemented with 10% FBS (Hyclone, Logan, Utah). For labile iron detection ARPE cells were stably transfected with a pcDNA3.1 plasmid with an IRE-GFP insert (gift of Drs. Sangwon Kim and Sol Snyder, Johns Hopkins) as a reporter for intracellular iron levels. These cells were named iron-reporting ARPE (iRPE) cells. Efficacy of labile iron chelation was tested by adding different concentrations of SIH to the iron-free MEM medium on iRPE cells and assessing decrease in GFP fluorescence as a measure of reduction in intracellular iron levels at the 24 h time point. Epifluorescence microscopy was performed with a Nikon TE-300 microscope (Nikon Inc., Japan) and SpotRT Slider camera (Diagnostic Instruments, Inc., Sterling Heights, Mich.) with ImagePro Plus software, version 4.1 (Media Cybernetics, Silver Spring, Md.).

Cell Death Induction and SIH Protection

To evaluate SIH's cytoprotective properties, SIH at different concentrations was applied to confluent ARPE-19 cells four hrs prior to the addition of H2O2, staurosporine or anti-Fas antibody. Hydrogen peroxide (30% H2O2 from Sigma, St. Louis, Mo.) at final concentration ranging from 1 to 5 mM, Staurosporine (1 mM solution from Sigma) at 100-500 nM final concentration or aFas antibody (Upstate-Millipore, Billerica, Mass.) at 1 μg/mL final concentration were mixed with the indicated concentrations of SIH immediately before applying to ARPE-19 cells. All reagents were dissolved in Minimal Essential Medium (MEM, Invitrogen) as indicated and were applied rapidly and uniformly following two washing steps in HBSS.

Viability Assays

Cell death was assayed after 24 hrs using the LDH Release Assay Kit (Roche, Basel, Switzerland). Cytotoxicity was calculated using the ratio between maximum LDH release in 2% Triton X100-treated cells and minimum LDH release in cells incubated in MEM. Visualization of cell death was performed using the LIVE/DEAD Viability/Cytotoxicity kit (Invitrogen).

For blue light irradiation experiments ARPE-19 cells devoid of endogenous lipofuscin were grown in complete medium (DMEM with 10% fetal calf serum and supplements) as previously described. At confluence the cells were allowed to accumulate A2E from a 10 μM concentration delivered in the culture medium over a 2 week period.
A2E/Blue Light ARPE-19 cells that had accumulated A2E were treated with SIH in MEM for 4 hrs unless otherwise indicated. The SIH/MEM was subsequently exchanged for DPBS, the cells were irradiated at 430 nm for 20 min and then returned to complete medium and incubated for 24 hrs. Variations on this paradigm included experiments in which exposure to SIH/MEM was continued during illumination at 430 nm and for 24 hr thereafter; and experiments in which cells were not pre-incubated with SIH but instead were treated with SIH/MEM beginning either immediately after irradiation and continuing for 24 hrs or beginning 1 hr after irradiation and continuing for 23 hrs. In all experiments controls included A2E-laden irradiated cells that were not treated with SIH, cells that received no treatment (A2E-free, non-irradiated, incubation with MEM in the absence of SIH) and cells treated only with SIH.
MTT Assay In blue light irradiation experiments cell death was assayed by the 3-(4,5-dimethylthiazol-2-yl)-2,5-diphenyltetrazolium bromide assay, a measure of the ability of healthy cells to cleave the yellow tetrazolium salt MTT to purple formazan crystals. Briefly, following the post-illumination incubation described above, 20 uL of MTT labeling reagent (Roche Diagnostics Corp, Indianapolis, Ind.) was added to 0.2 mL of culture medium in each well and after a 4 hr incubation, the labeling reagent was replaced with 200 uL of solubilization solution for an overnight incubation. After centrifugation at 13,000 rpm for 2 min, supernatants were measured spectrophotometrically. A decrease in the absorbance (570 nm) of reduced MTT was indicative of diminished cellular viability.
Rhodamine 123

Intracellular ROS generation was measured in cultured cells by using the fluorescent probe dihydrorhodamine 123 (DHR123). Mitochondria were localized with Mitotracker Red 580 (Molecular Probes, Eugene, Oreg.). After 30 min of staurosporine exposure with our without SIH, cells were incubated with staurosporine +/−SIH in the presence of 10 μM DHR123 and 2 μM Mitotracker Red 580 at 37° C. for 15 min. DHR fluoresces and localizes to mitochondria when oxidized by ROS to the positively charged rhodamine 123[33]. Mitotracker dye passively diffuses across the plasma membrane and specifically accumulates in active mitochondria.
Mitochondrial Fractionation For mitochondria purification ARPE-19 cells were cultured in sterile Nunclon-75 flasks (Nunc, Denmark) until confluent and treated for 24 h with SIH, $H_2O_2$, or staurosporine as described above. All reagents were applied following two washing steps in MEM as described above. After 24 h treatment cells were washed twice in ice-cold phosphate-buffered saline (PBS), harvested by scraping with Sarstedt Cell Scrapers and homogenized using Dounce homogenizer in 2 mL of isolation solution containing 40 mg digitonin/100 mL buffer (17 mM MOPS, pH 7.4 with 250 mM Mannitol and 2.5 mM EDTA) and protease inhibitors (Complete™ from Roche). Then cells were transferred to a tube with 0.6 mL 2.5× Mannitol-Sucrose buffer (525 mM Mannitol, 175 mM Sucrose, 125 mM Tris, 12.5 mM EDTA, pH 7.4) containing protease inhibitors and subjected to sequential fractionation according to Qproteome Mitochondria Isolation kit (Qiagen) manufacturer protocol. For higher purity preparation, the crude mitochondria pellet was further separated in Purification Buffer/Disruption Buffer interface as described in Qproteome handbook. Mitochondria fractions were lysed with 2% CHAPS in Tris buffered saline (25 mM Tris, 0.15 M NaCl; pH 7.2) and vortexed for 1 min following by centrifuging at high speed for 2 min. The supernatants containing soluble mitochondrial proteins were analyzed by BCA Protein Assay. The presence of mitochondria proteins in the extracts was confirmed by Western immunoblotting with anti-Complex V antibodies.
Western Analysis For Western immunoblotting analysis equal amounts of total protein from cell lysate or mitochondria protein extracts (as determined using BSA Protein Assay Kit from Pierce) were separated onto gradient 4-12% polyacrylamide gels (Novex) and transferred onto nitrocellulose membrane (Invitrogen). The membrane was blocked with 4% fat-free milk in Tris-0.05% Tween-20 for 1 h at RT, probed with primary antibody (rabbit anti-DNP from Zymed/Invitrogen or mouse anti-Complex V subunit alpha from MitoSciences), washed in TBE-0.05% Tween-20 and incubated 2 h at room temperature with horseradish peroxidase-conjugated secondary antibody (Pierce). For anti-DNP blotting nitrocellulose membrane dried completely at room temperature, equilibrated in 20% methanol-80% TBS for 5 minutes, pre-washed with 2N HCl and incubated in a solution of 0.5 mM 2,4-dinitro-phenylhydrazine (Sigma) in 2N HCl for 5 minutes. The membrane was then washed three times in 2N HCl and five times in 50% methanol (ref: Biol. Proced. Online 2000; 2:39-45, Post-Electrophoretic Identification of Oxidized Proteins. Craig C Conrad et al). Anti-GAPDH antibodies were used as loading control for total protein extracts. Detection was performed using Hyperfilm (Amersham Biosciences, Buckinghamshire, UK) and SuperSignal West Femto™ substrate (Pierce, Arlington Heights, Ill., USA), as described by the manufacturer. Quantification was performed by densitometry using ImageQuant TL software (Amersham Biosciences).
Statistical Analysis for LDH and MTT Assays Within each experiment, the mean absorbance value of duplicated wells was obtained. We then calculated the mean and standard errors for each condition across replicate experiments conducted on different days. Across replicates on different days, experimental samples were compared to controls using the two group t-test. The n was either 3 or 4 for each experimental condition. All statistical analysis was performed on the statistical software SAS (version 9.1, SAS Institute, Inc., Cary, N.C.).

Example 1

SIH Effectively Chelates Labile Iron in Cultured ARPE-19 Cells

To quantify the labile iron pool, an iron-reporting RPE cell line (iRPE) was first generated, wherein fluorescence green fluorescent protein reflects labile iron levels. This was accomplished by making a stable cell line with the plasmid IRE-GFP (gift of Sangwon Kim and Sol Snyder). The iron responsive element (IRE) sequence in the 5' untranslated region of the mRNA is bound by iron regulatory proteins only when labile iron levels are low, leading to inhibition of GFP translation. The fluorescence of iRPE cells treated with different concentrations of SIH for 24 h was determined (FIG. 2). While at 1 mM SIH GFP fluorescence decreased slightly, at SIH concentrations 3 and 10 μM it decreased significantly. Surprisingly, at high concentrations of SIH (50 and 100 μM) GFP fluorescence was close to the level of untreated control.

In addition to decreasing the iRPE fluorescence levels in iron-free MEM medium, SIH also decreased the fluorescence when used in the iron-containing medium DMEM-F12 with 10% fetal calf serum.

Example 2

SIH Protects ARPE-19 from Cell Death Induced by Lethal Doses of $H_2O_2$

Figure 3:
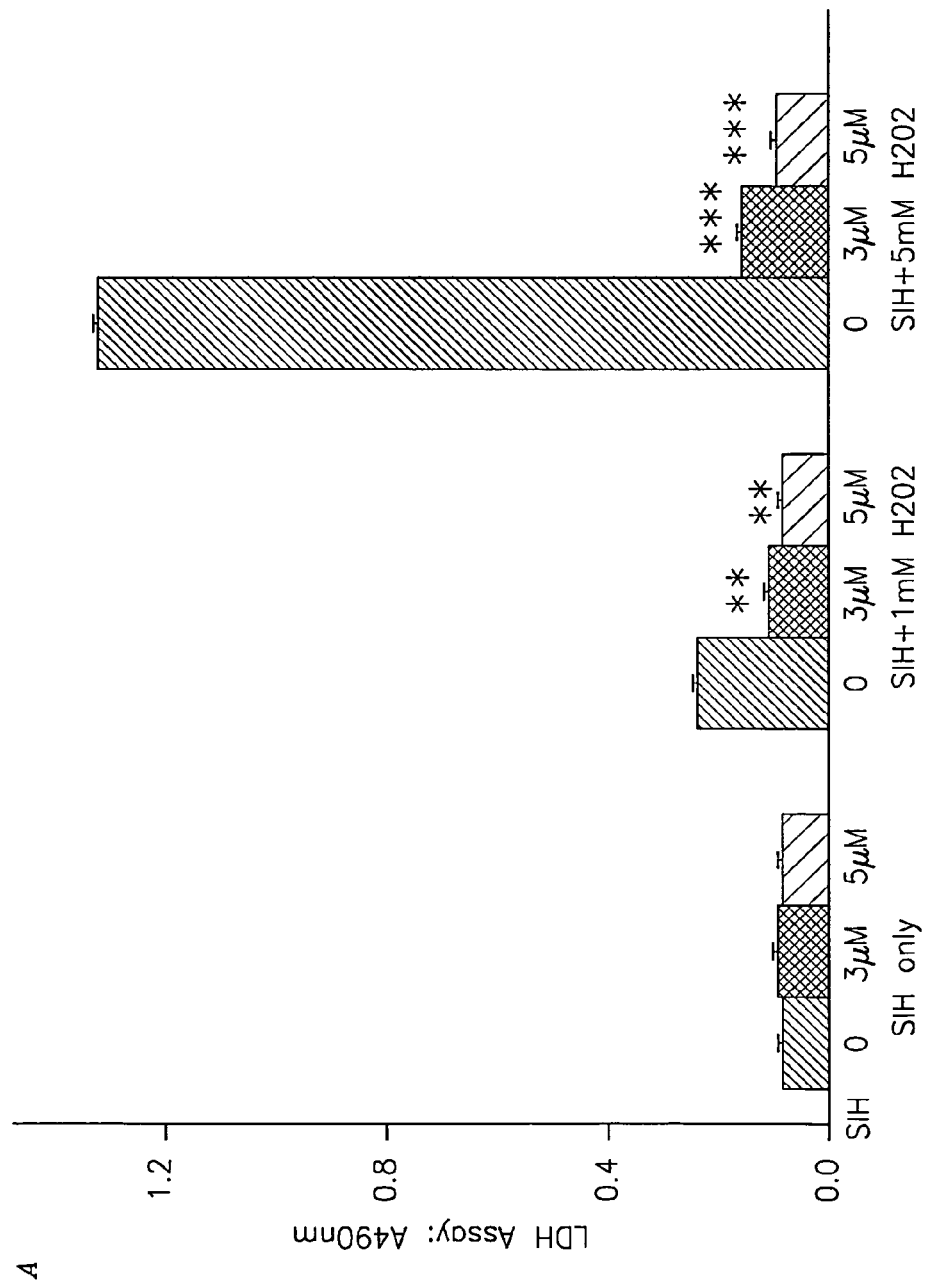
FIG. 3 shows a graph of cytotoxicity measured by LDH release into the medium showing SIH-protection of ARPE-19 cells against H2O2-induced cell death. (A) Cytotoxicity of 1, 2, and 5 mM H2O2 exposure for 24 hrs when co-incubated 4 hr before and during H2O2 exposure with the indicated concentrations of SIH.  indicates $p<0.01$ relative to no SIH at the corresponding H2O2 level. * $p<0.001$ (B) Fluorescence photomicrographs of ARPE-19 cells labeled using the LIVE/DEAD Assay: ARPE-19 cells were treated for 24 h with HBSS (control), 5 mM $H_2O_2$ alone, or 5 mM H2O2 with or without SIH as indicated. Red indicates dead cells as detected by ethidium bromide homodimer fluorescence. Green indicates live cells as detected by calcein fluorescence.
Figure 3:
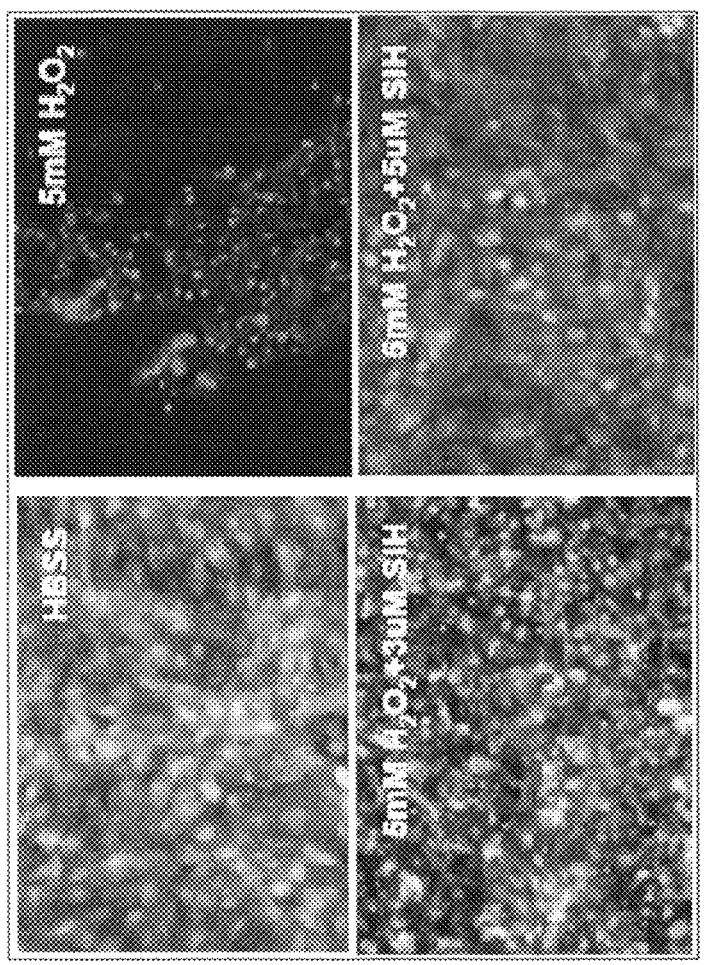
Figure 4A:
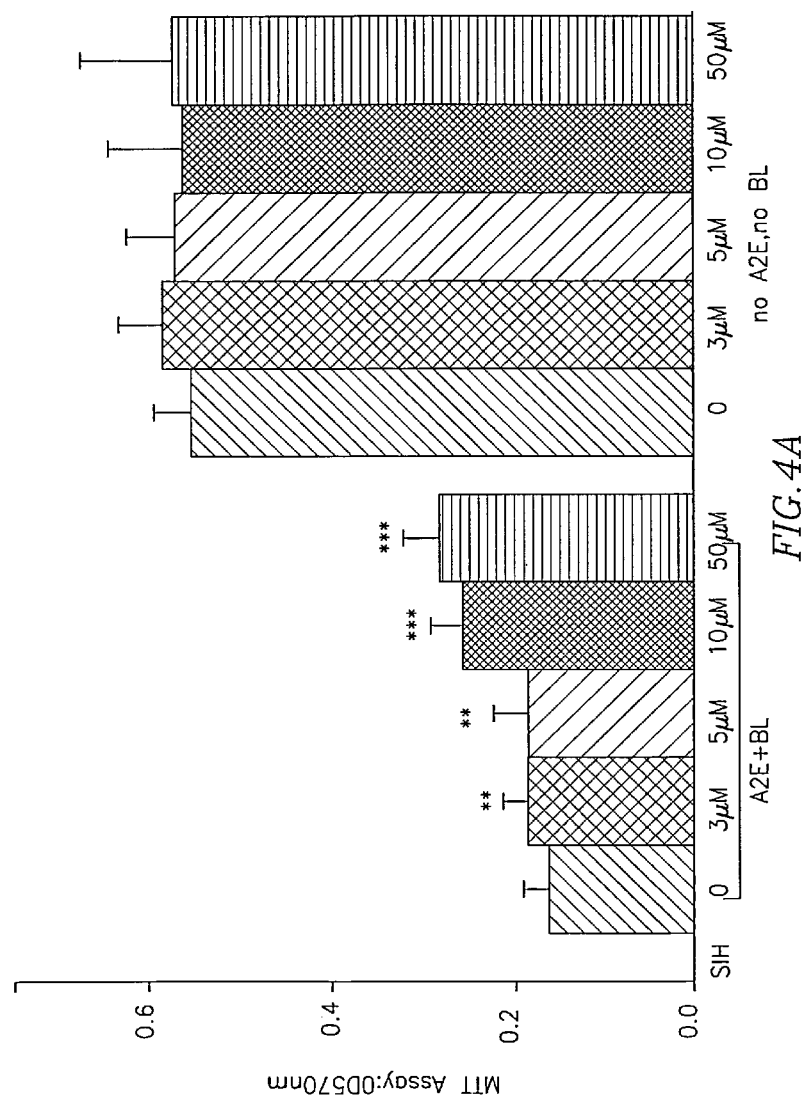
FIG. 4 shows the protective effects of SIH against cell death induced by blue light in the presence of A2E. Graphs show ARPE-19 cell viability measured by the MTT assay. Increased absorbance indicates increased viability. (A) Cells were incubated with the indicated concentrations of SIH-MEM for 4 h, irradiated with blue light for 20 min in DPBS-SIH, and incubated in MEM-SIH for 24 hr before performing MTT assay. (B) Cells were pre-treated with MEM-SIH for 4 h, irradiated with blue light for 20 min in DPBS and incubated in MEM for 24 h. (C) Cells were irradiated by blue light for 20 min in DPBS and SIH-MEM was applied immediately after irradiation and maintained for 24 hrs. (D) Cells were irradiated with blue light for 20 min in DPBS and SIH-MEM was applied 1 h after irradiation and maintained for 23 h before performing MTT assay. For all graphs, relative to no SIH, * $p<0.05$,  $p<0.01$, * $p<0.001$.
Figure 4B:
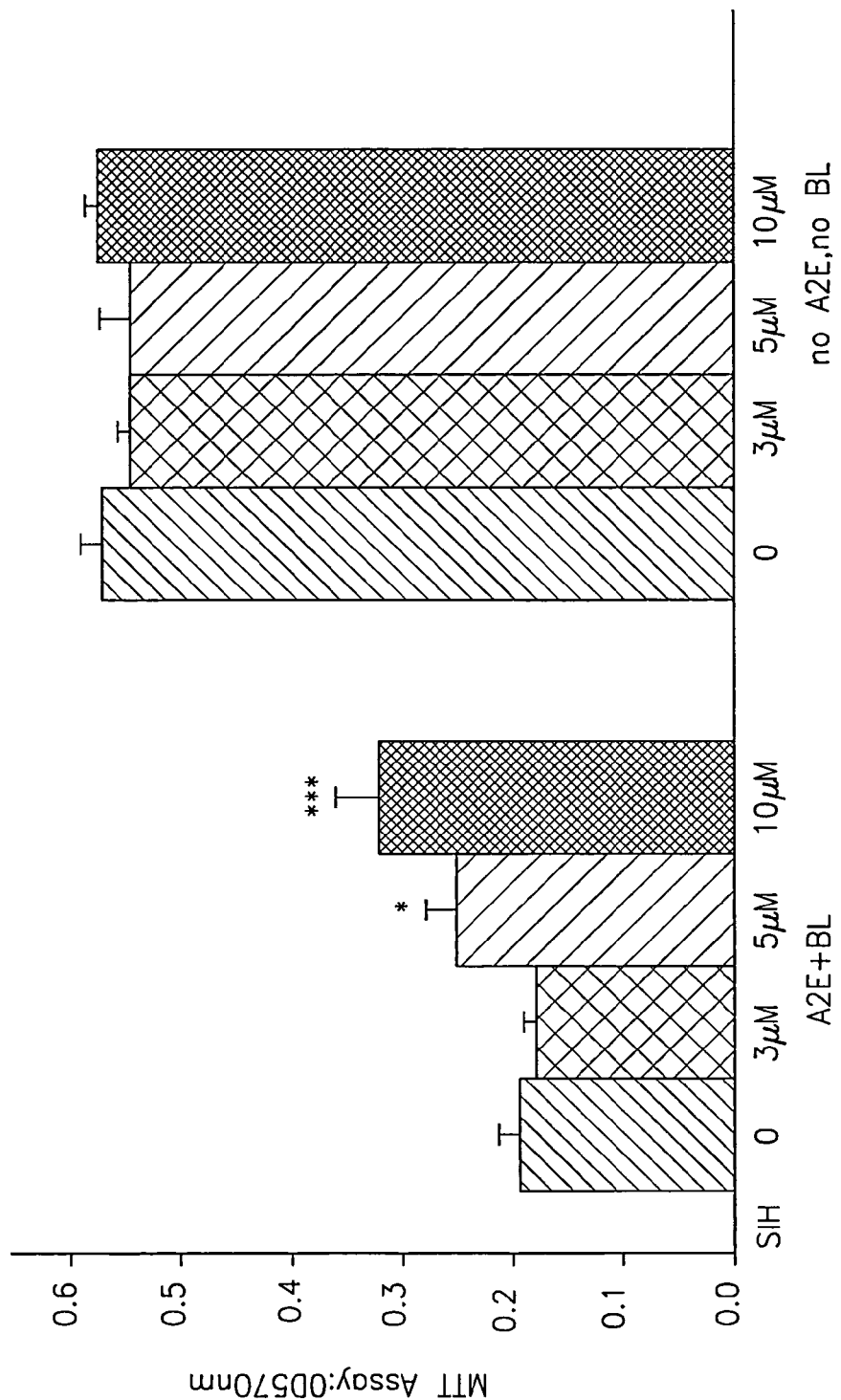
Figure 4C:
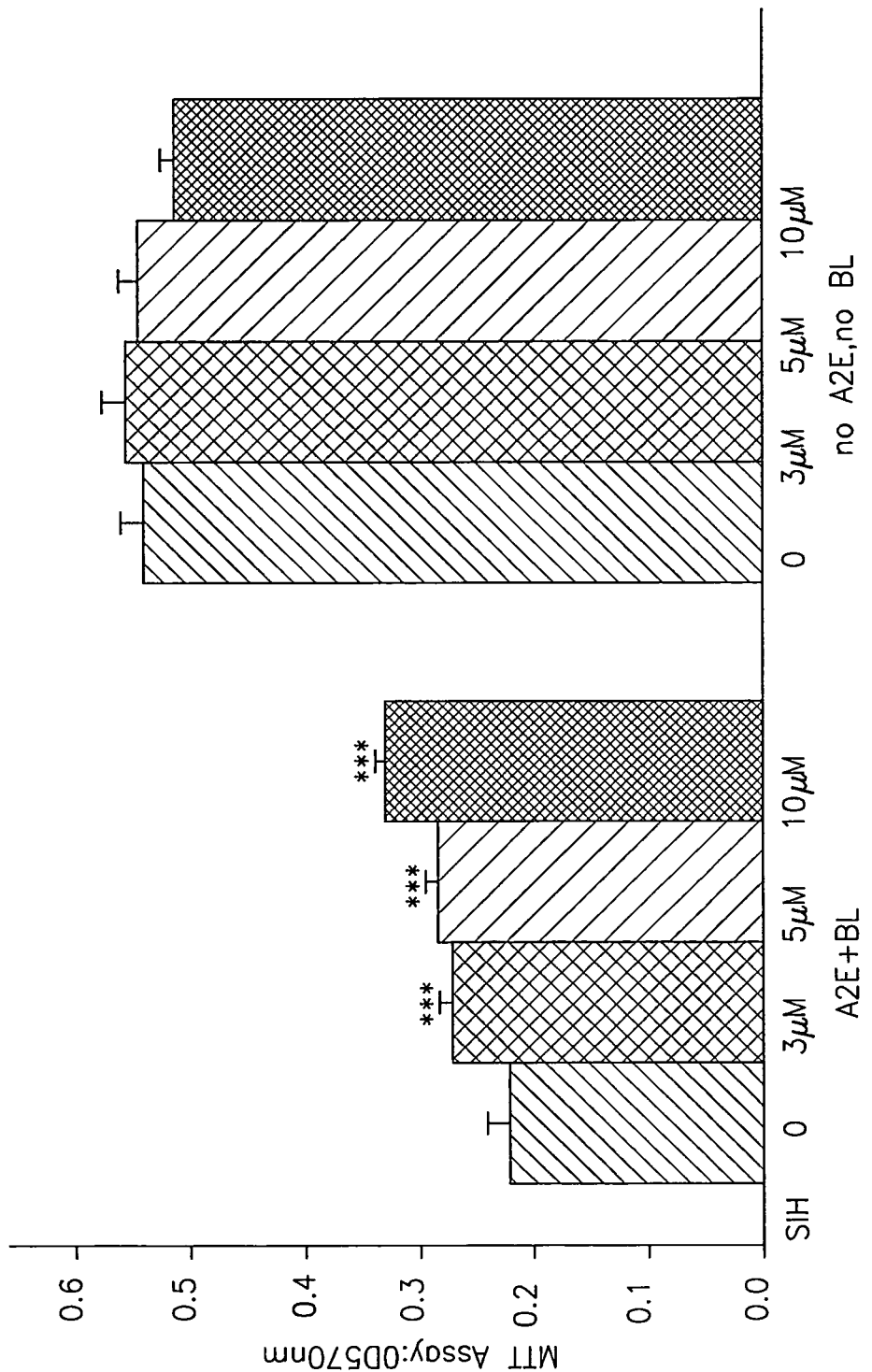
Figure 4D:
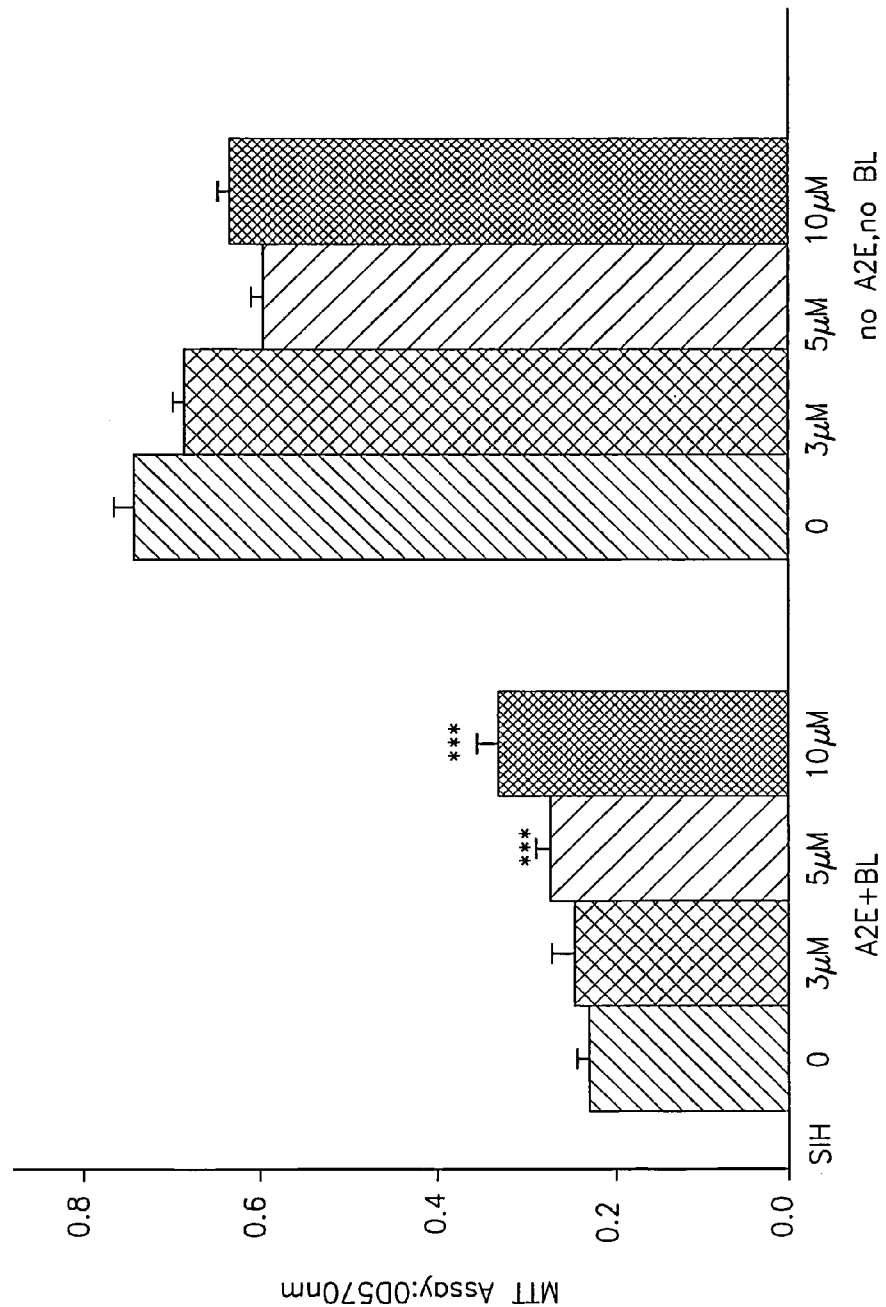

ARPE-19 cells treated with 1, 2 and 5 mM H2O2 for 24 h exhibit increasing amounts of cell death (FIG. 3). 5 mM $H_2O_2$ causes 100% cell death assessed by both the LDH release assay and the fluorescent Live/Dead assay. When cells were treated with 5 or 10 µM SIH before applying H2O2, followed by treatment by H2O2 mixed with SIH, the 5 mM H2O2 cytotoxicity was completely abolished. The viability of cells detected by both assays correlated well in all experiments. Diminished cytoprotection was observed when SIH was applied to cells together with $H_2O2$ but without SIH pre-treatment, and no protection was found when SIH was applied to the cells 1 h after H2O2 or after the SIH had been pre-incubated with ferric ammonium citrate in a 2:1 molar ratio (data not shown). To rule out the possibility of chemical interaction between SIH and H2O2, we examined UV/VIS spectra of both chemicals and its mixture, and did not detect any changes in spectroscopic properties of SIH—H2O2 mixture compared with SIH and H2O2 alone.

Example 3

SIH Provides Cytoprotection Against Cell Death by Irradiation with Blue Light in the Presence of A2E Human RPE cells accumulate lipofuscin with age. A major component of this lipofuscin is A2E, a blue-light absorbing compound that we have shown to potentiate blue light-induced photo-oxidative stress and apoptosis of ARPE-19 cells. When A2E loaded ARPE-19 cells were treated with SIH before, during, or even as late as 1 hr after blue light exposure, cell viability was increased (FIG. 4). The greatest increase in cell viability was observed when SIH was present before, during, and after light exposure, but partial protection was still evident when SIH was applied 1 hr after light exposure. No SIH-mediated toxicity was observed in cells incubated with SIH but not exposed to A2E or blue light.

Example 4

SIH Protects ARPE-19 Against Fas-Induced Apoptosis

Figure 5:
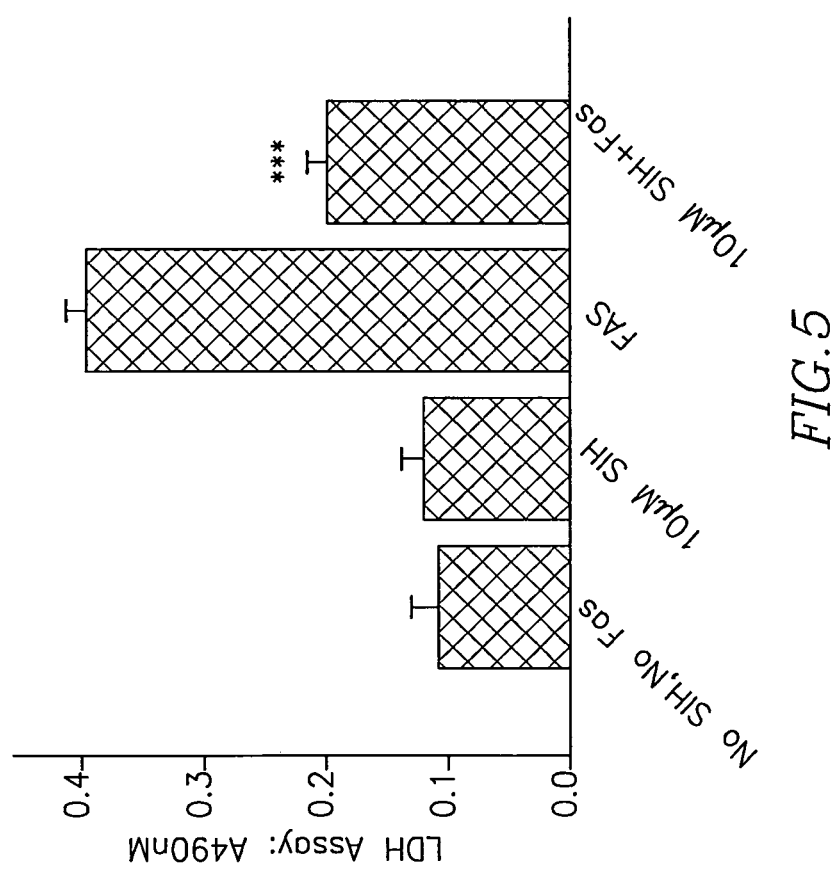
FIG. 5 shows LDH release into the medium following aFas treatment with or without SIH as indicated. $p<0.001$ relative to Fas without SIH.

Fas is a cell surface receptor known to initiate cell death when activated in a number of cell types, including ARPE-19 cells. The receptor can be activated by exposure to an anti-Fas antibody (aFas) that acts like Fas-ligand. Treatment of ARPE-19 cells with SIH beginning 4 hrs before treatment with aFas reduced cell death caused by Fas activation, as indicated by the LDH release assay (FIG. 5).

Example 5

SIH Protects ARPE-19 from Cell Death Induced by Staurosporine

Figure 6:
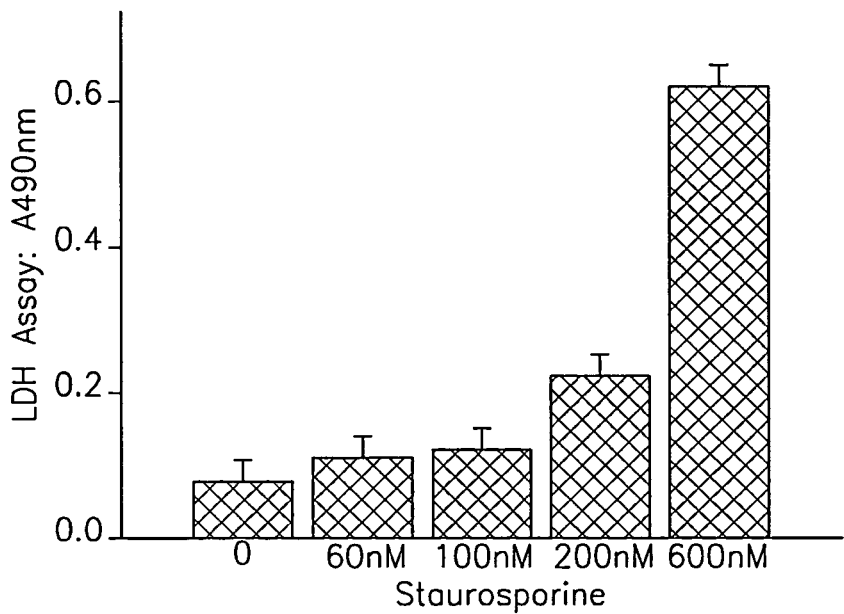
FIG. 6 shows an analysis of the protective effects of SIH against staurosporine-induced cell death. (A) Graph of LDH release following exposure of ARPE-19 cells to varying concentrations of staurosporine. Relative to no staurosporine,  $p<0.01$, * $p<0.001$. (B) Graph of LDH release following exposure of ARPE-19 cells to 200 nM staurosporine plus different concentrations of SIH. Relative to staurosporine with no SIH, ** indicates $p<0.01$. (C) Fluorescence photomicrograph of cells labeled with the LIVE/DEAD assay following treatment with staurosporine and/or SIH as indicated.
Figure 6:
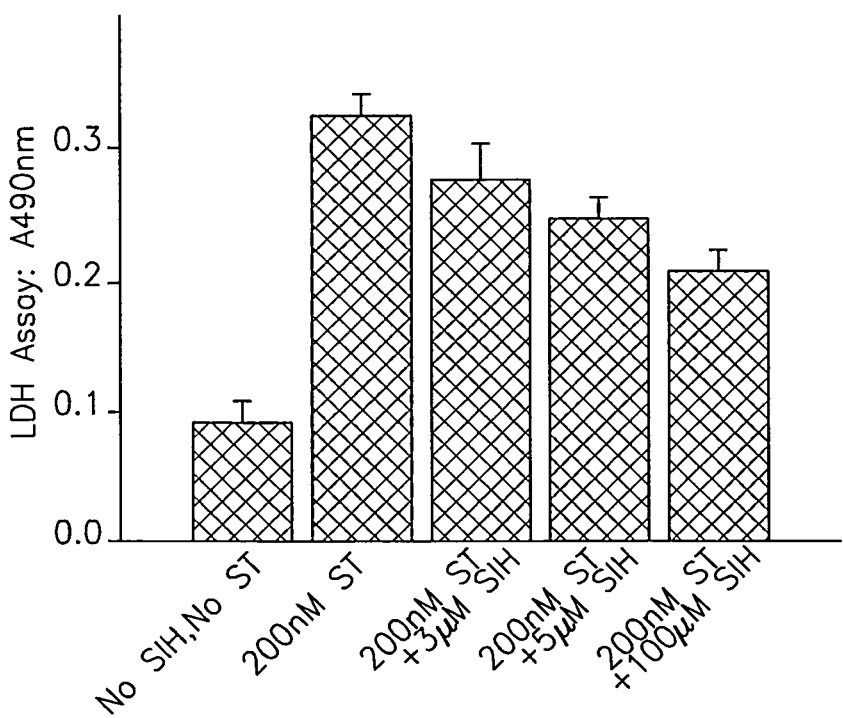
Figure 6:
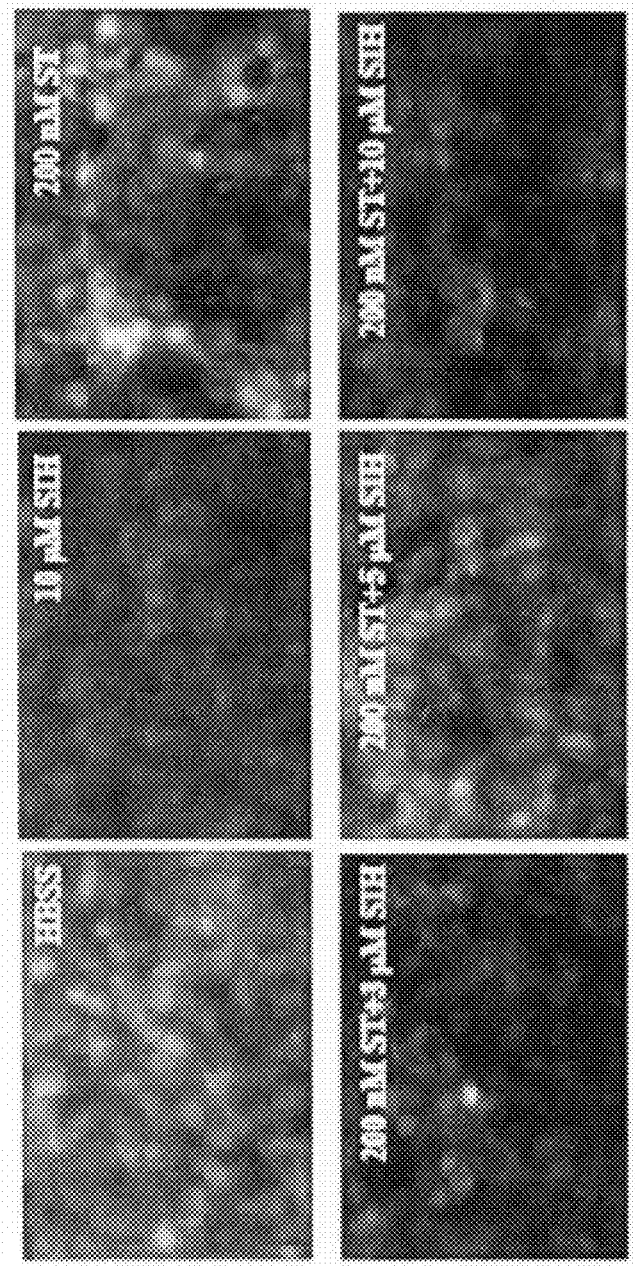

Staurosporine at concentrations of 100-500 nM causes apoptosis of ARPE-19 cells. When tested, 200 nM and 500 nM staurosporine caused significant cell death (FIG. 6A). When SIH was applied to cells 4 h before treatment with 200 nM staurosporine (FIG. 6B) or 500 nm staurosporine (not shown), and was present through 24 h of staurosporine treatment, cell viability was increased in an SIH concentration-dependent manner (FIG. 6B). The greatest SIH cytoprotective effect was achieved at 10 µM SIH. The visualization of dead cells using the live/dead fluorescent imaging correlated with data from LDH release assay (FIG. 6C). Several red (dead) cells were visible in each field from cells treated with staurosporine alone, but very few or none were present in cultures treated with staurosporine plus 5 or 10 µM SIH.

Example 6

SIH Decreases Mitochondrial ROS Production Induced by Staurosporine Treatment

Figure 7:
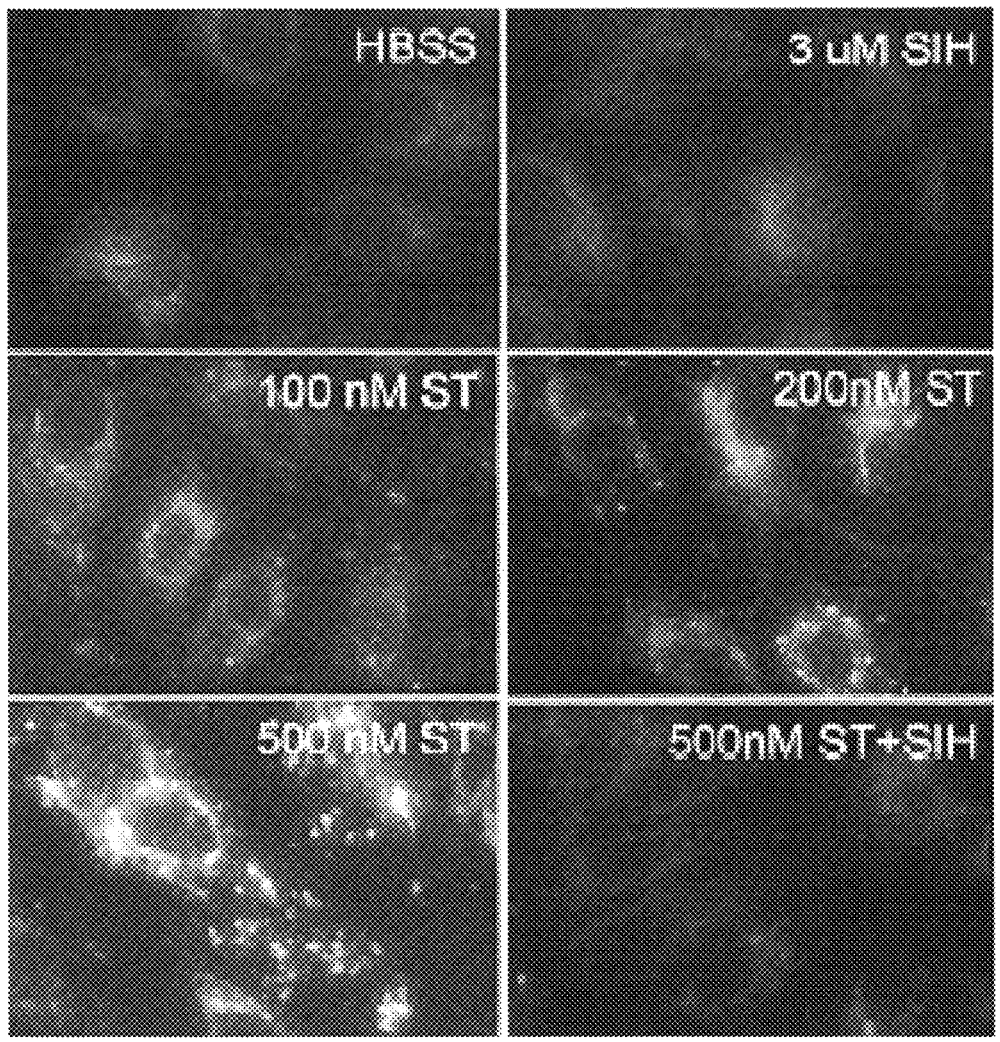
FIG. 7 shows fluorescence photomicrographs of ARPE-19 cells. Level of ROS generation is detected by dihydrorhodamine 123 (green fluorescence) in cells treated with staurosporine and/or 3 µM SIH as indicated. Mitotracker dye (red fluorescence) indicates location of mitochondria.

Mitochondrial ROS production is an important component of staurosporine's cell death mechanism15. To test whether iron contributes to this ROS production, and whether a decrease in mitochondrial ROS might be a mechanism of SIH protection, ROS were detected with rhodamine 123 after 30 min of staurosporine treatment. In the presence of ROS, non-fluorescent dihydrorhodamine 123 is converted into highly fluorescent rhodamine 123. There was increased fluorescence of rhodamine 123 in ARPE-19 cells treated with 200 nM staurosporine for 30 min followed by incubation with dihydrorhodamine 123 for 15 min (FIG. 7). A greater increase in fluorescence, in addition to more non-mitochondrial fluorescence, was observed in cells treated with 500 nM staurosporine. In the presence of 3 µM SIH, staurosporine-induced rhodamine 123 fluorescence was diminished.

Example 7

SIH Decreases Levels of Carbonyls in Mitochondria Proteins

Figure 8:
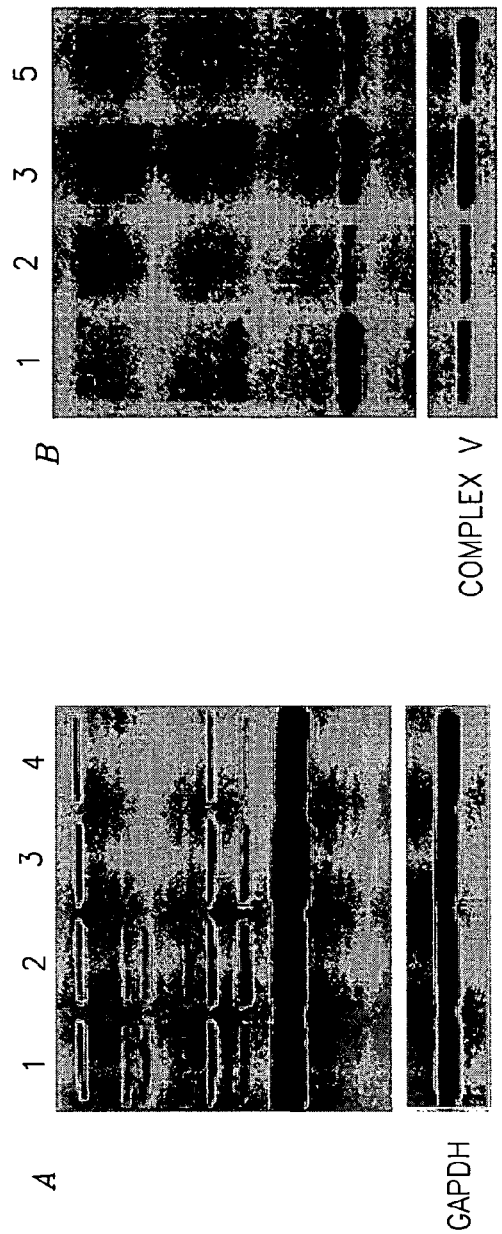
FIG. 8 shows Western analysis of protein extracts of total cell lysates and mitochondria-enriched fractions obtained from ARPE-19 cells treated with 5 mM H2O2 (lanes 1,2) or 200 nM staurosporine (lanes 3,4) in the presence (lanes 2,4) or absence (lanes 1,3) of 5 µM SIH. Top panel—detection of multiple bands containing protein carbonyls in total protein extracts, bottom panel—loading control labeled with an anti-GAPDH antibody. top panel—detection of multiple bands containing protein carbonyls in protein extracts of mitochondria-enriched fractions, bottom panel—anti-complex V, a mitochondria-specific protein. Graph showing densitometry reflecting the ratio of all carbonyl bands in each lane to the GAPDH or complex V band. Each bar represents the densitometry ratio from the Western lane above the bar.
Figure 8:
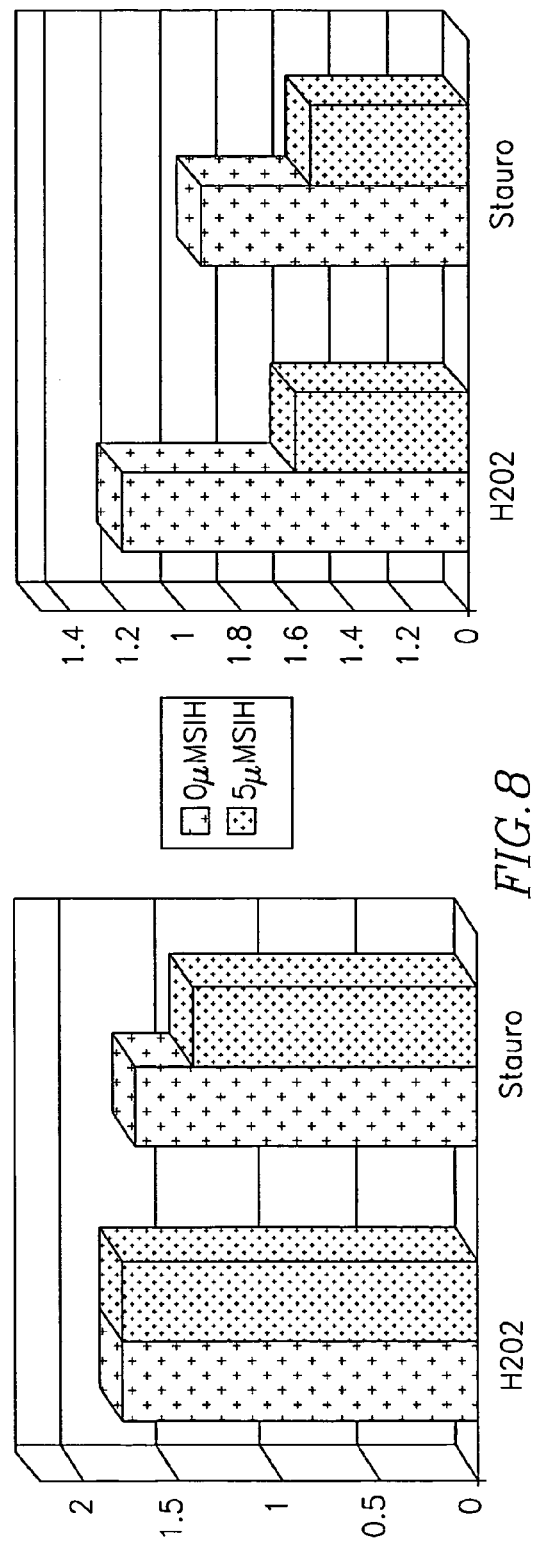

Since ROS generation was found to be an early response of ARPE-19 cells upon anti-staurosporine treatment, and mitochondrial ROS production is thought to be an important component of staurosporine signaling15, the question of whether mitochondrial proteins undergo oxidative damage following staurosporine treatment, and whether SIH can prevent this wastested. To test for oxidative damage to mitochondrial proteins, the formation of protein carbonyls was assessed using western immunoblotting analysis of total protein extracts from cell lysates and from mitochondria-enriched fractions. While carbonyl levels in untreated cells were variable, SIH did not affect carbonyl levels in total protein extracts treated with H2O2. A small decrease in carbonyls was observed in total protein extracts in the presence of SIH in staurosporine-treated cells, and a more pronounced decrease in carbonyl levels was found in mitochondria-enriched fractions in cells treated for 24 h with either staurosporine or H2O2 (FIG. 8).

Having described preferred embodiments of the invention with reference to the accompanying drawings and Examples, it is to be understood that the invention is not limited to the precise embodiments, and that various changes and modifications may be effected therein by those skilled in the art without departing from the scope or spirit of the invention as defined in the appended claims.

What is claimed is:

1. A method of alleviating symptons of, reducing incidence of, improving symptoms of, or amelioration of the dry form of age-related macular degeneration in a subject, comprising administering topically or via injection, to an eye of a subject in need thereof an ophthalmic composition comprising a therapeutically effective amount of salicylaldehyde isonicotinoyl hydrazone (SIH), thereby alleviating symptons of, reducing incidence of, improving symptoms of, or amelioration of said dry form of age-related macular degeneration.

2. The method of claim 1, whereby the step of administering to said subject with said composition is capable of reducing the concentration of iron in said subject.

3. The method of claim 1, whereby said salicylaldehyde isonicotinoyl hydrazone (SIH) is administered at a dose that results in a tissue concentration of between about 1 to about 7 µM.

* * * * *